United States Patent [19]

Miano

[11] Patent Number: 4,802,245
[45] Date of Patent: Feb. 7, 1989

[54] EAR PROTECTOR

[76] Inventor: Richard J. Miano, 1860 Alamoana Blvd. Suite 1202, Honolulu, Hi.

[21] Appl. No.: 909,910

[22] Filed: Sep. 19, 1986

[51] Int. Cl.⁴ .............................................. A42B 3/00
[52] U.S. Cl. .......................................... 2/209; 2/68
[58] Field of Search ............ 2/209, 208, 423, 425, 2/68

[56] References Cited

U.S. PATENT DOCUMENTS

| | | |
|---|---|---|
| 1,274,842 | 8/1918 | Basch .................................. 2/208 |
| 2,021,144 | 11/1935 | Beck .................................... 2/209 |
| 2,405,326 | 8/1946 | Plotsky ................................ 2/209 |
| 2,738,514 | 3/1956 | Gondell ............................... 2/209 |
| 2,929,071 | 3/1960 | Sterling et al. ..................... 2/68 |
| 3,454,962 | 7/1969 | Hind .................................. 2/209 X |
| 3,728,741 | 4/1973 | Lepor ................................. 2/209 |
| 4,551,861 | 11/1985 | Marchello ......................... 2/209 X |

Primary Examiner—Louis K. Rimrodt
Assistant Examiner—J. L. Olds
Attorney, Agent, or Firm—Wolf, Greenfield & Sacks

[57] ABSTRACT

An ear protection device made of a molded band of rubber or other elastomeric material which is formed with a cup-like member to cover the ear and seal against the head. The band is shaped to run across the user's forehead in the front, stepping down over the ears and continuing at ear level around the back of the user's head. The inside of the cup-like member may be filled with an absorbent material, to capture any water which may leak in; when used by skiers, such material, if used, provides an extra measure of insulation. The profile of the protector may be kept relatively thin by using a cup-like member contoured to mate readily with the bony regions surrounding the ear.

3 Claims, 1 Drawing Sheet

EAR PROTECTOR

FIELD OF THE INVENTION

This invention relates to the field of ear protection devices and, more particularly, to an ear protection device for swimmers, skiers and others. When worn by a swimmer, it protects his or her ears against the incursion of water and resulting infection. When worn by a skier, it protects agains the incursion of cold air against the ears.

BACKGROUND OF THE INVENTION

It has long been appreciated that in certain types of activities such as swimming and skiing, a person's ears are vulnerable. One of the hazards of swimming is that water can enter and then remain in a swimmer's outer ear. This not only can create considerable discomfort due to the motion of the water against the eardrum, but also can result in infection of the ear by organisms present in the water. Additionally, certain ear problems such as chronic otitis media are treated by insertion in the eardrum of a small grommet to provide an air passage across the eardrum. The danger of infection by water-carried organisms is particularly acute for persons so treated. In a totally unrelated activity, skiing, one's ears are one of the first body organs to be affected by the cold weather and one of the first body parts to register discomfort from the cold.

Various devices have been available in the past for use by swimmers to bar the entry of water into their ears. The most common of such devices are plugs of different shapes, made of materials such as rubber and plastic. It is difficult, however, to create a plug which fits well (i.e., snugly and comfortably) and also is not easily dislodged. Bathing caps are also sometimes employed for ear protection, but they are a rather unsatisfactory solution since it is virtually impossible to seal the aperture against water. Indeed, bathing caps are not normally intended by their makers to be used for ear protection. Confidence that the protective device will perform as required and will not dislodge is particularly important for a competitive swimmer since he or she will not want to break stroke to adjust an earplug or bathing cap which is working loose. The difficulty of simultaneously satisfying these varied objects is accentuated by the fact that human ears occur in an almost infinite variety of shapes and sizes. To satisfy the needs of the general populace without incurring the manufacturing and marketing overhead of supplying plugs in a wide range of sizes and shapes is challenging. Compromises are often made to reduce the number of earplug sizes to a manageable handful. Consequently, patients in whose eardrums the aforementioned grommets have been placed often find it necessary to have earplugs custom-molded to fit snugly in their ears. Moreover, as many of such patients are young children, such plugs may have only a relatively short lifetime; as the child grows, he or she outgrows a custom-molded earplug. Not only does this require that a new plug or plugs be made periodically, but it also means that any given earplug is maximally effective only briefly.

The prior ear protection devices, particularly plug type devices, may also feel unnatural and appear unattractive. If the user preceives the appearance to be unattractive, he or she may choose to refrain from using the protector, leading to unnecessarily increased danger of infection.

Skier's have protected their ears with earmuffs and with knit caps and other types of hats having ear covering portions. These measures, however, generally provide an ineffective seal against the flow of cold air.

Accordingly, it is an object of the present invention to provide an ear protection device which is useable and effective to seal the ear from external fluids.

Another object is to provide an ear protector which can be provided for the populace in only a relatively small number of unique sizes.

A further object of the invention is to provide an ear protection device for swimmers, which device is not easily dislodged from the ear.

Still another object of the invention is to provide an ear protection device which can be made aesthetically attractive.

Yet another object is to provide an ear protection device which is comfortable to wear.

SUMMARY OF THE INVENTION

These and other objects of the invention are achieved by an ear protection device made of a molded band of rubber or other elastomeric material which is formed with a cup-like member to cover the ear and seal against the head. The band is shaped to run across the user's forehead in the front, stepping down over the ears and continuing at ear level around the back of the user's head. The inside of the cup-like member may be filled with an absorbent material, to capture any water which may leak in; when used by skiers, such material, if used, provides an extra measure of insulation. The profile of the protector may be kept relatively thin by using a cup-like member contoured to mate readily with the bony regions surrounding the ear; this is also useful to ensure a good seal against the jaw.

The ear protector may be made in attractive colors and may be imprinted or embossed with designs to further enhance aesthetic appeal.

The invention is pointed out the with particularity in the appended claims. The foregoing objects, features and advantages of the invention may be better understood by referring to the detailed description below, which should be read in conjunction with the accompanying drawing.

DETAILED DESCRIPTION OF A PREFERRED EMBODIMENT

Figure 1:
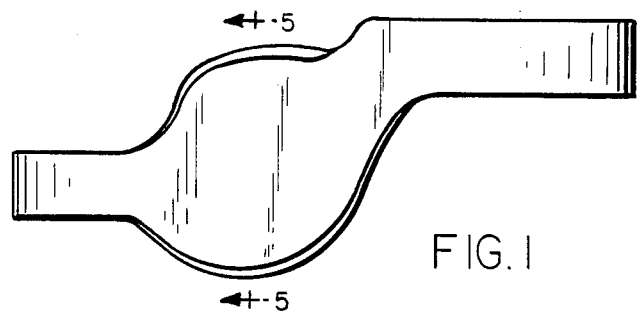
FIG. 1 is a side view of the ear protector of the present invention.
Figure 2:
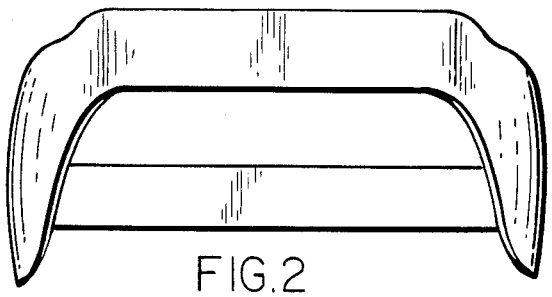
FIG. 2 is a front view of the ear protector of FIG. 1.
Figure 3:
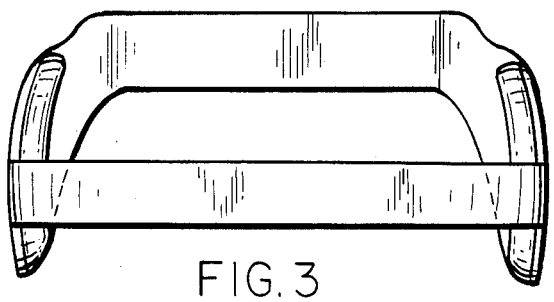
FIG. 3 is a rear view of the ear protector of FIG. 1.

Side, front and back views of the ear protector 10 of the present invention are shown, respectively, in FIGS. 1-3. The device comprises a band 11 having a first portion 12 of dimensions which comfortably fit across a user's forehead, an ear-covering section 14 depending downward therefrom and a rear portion 16 connecting the ear-covering portions and dimensioned to comfortably fit across the back of the user's head. The preferred material for the device 10 is a rubber or other elastomeric composition which is sufficiently resilient as to hold the ear-covering portions 14 over the user's ears without applying so much pressure to the user's head as to be uncomfortable. These devices may be made in just a few different sizes to cover the vast majority of the populace, since there is no need to match the intricate details of the interior of the ear structure of the user.

Figure 4:
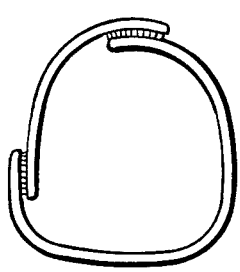
FIG. 4 is a top plan view of a second embodiment of the invention.

Optionally, the invention may be made adjustable to the size of the user's head. Adjustability may be added to the forehead-spanning portion 12 or the head back spanning portion 16. Suitable fastening elements include Velcro brand touch fasteners from Velcro Industries, Inc., Manchester, N.H., or snap-fastener assemblies, such as are conventionally used to adjust chin straps of bathing caps. FIG. 4 shows an embodiment having adjustable forehead and head back straps, though it is of course possible to incorporate only one point of adjustment. As illustrated, forehead strap 12 and back strap 16 each carry one part of a Velcro touch fastener (22 and 24, respectively); the mating portion of the fastener 22 is carried on a facing portion of back strap 16, while the mating portion of fastener 24 is carried on or adjacent to a facing portion of ear-covering section 14. Of course, other fastening arrangements are also practical; the foregoing is intended only as an example.

Figure 5:
FIG. 5 is a sectional view of the ear-covering region 14 of the device of FIG. 1, taken along the line 5—5 and showing one way the ear-covering region may be constructed.

In addition to the single layer construction of Figs. 1–4, which is possible, the invention may also be constructed with a multi-layer ear covering. Such a construction is shown in FIG. 5, which depicts a cross-sectional view of the ear-covering portion of the protector, from the front of the user's head, along section lines 5—5 of FIG. 1. The outer layer of the assembly is the ear-covering portion 14 of the band 11. A molded, resilient rubber or foam cup 32 is secured to the band 11. The cup has a recessed central region 33A and a contoured rim 33B. The lower portion 34 of the rim 33B, which is intended to interface with the area of the head at the base of the ear (i.e., adjacent the jaw) is of greater depth than the upper portion 35, which bears against a part of the head which is relatively stationary with respect to the ear. The interior of the cup may contain a layer of an absorbent material 38, such as sponge or cotton, or trap any water which may leak in and to provide additional thermal insulation.

Figure 6:
FIG. 6 is another sectional view taken along line 5—5 and showing an alternative embodiment for the construction of the ear-covering region.

The cup surrounding the ear may also be formed by affixing an annular rim to the member 14, as shown at 42 in FIG. 6. The difference between this embodiment and that of FIG. 5 is that the area interior to rim 42 is partially filled by the rubber cup 32 in FIG. 5, while it is open in FIG. 6. Of course, the absorbent material 38 may be used in both embodiments.

The cup 32 or annular rim 42 may be made of the same material as or a different material from band 11. If the same material is used, a one-piece molding may be made for both. The two pieces may be made of different materials, also, and fastened in a manner appropriate for the materials which have been employed. The use of two different materials may be advantageous, so that a softer, more pliable and resilient material may make direct contact at the ear. Additionally, the cup 32 or annular rim 42 may be formed of multiple layers, such as a layer of a pliable foam covered by a sealed skin or a core of a softer foam covered by a layer of firmer foam. Further, parts of the protection device may be covered by a cloth outer layer for greater comfort.

Having thus described a basic embodiment of the invention and a number of alternative embodiments or variations thereof, it is apparent that various other alterations, modifications and improvements will readily occur to those skilled in the art. Such obvious alterations, modifications and improvements, though not expressly described herein, are nevertheless intended to be implied and are within the spirit and scope of the invention. Accordingly, the foregoing discussion is intended to illustrative only, and not limiting; the invention is limited and defined only by the following claims and equivalents thereto.

What is claimed is:

1. An ear protector for use by a swimmer, comprising:
   a. a first band of dimensions which fit comfortably across a user's forehead;
   b. for each ear, an ear-covering member depending downwardly from said band;
   c. a second band linking the ear-covering members, such second band attaching to each ear-covering member proximate the portion thereof which covers the bottom of the user's ear and dimensioned to fit comfortably across the back of the user's head; and
   d. a resilient rim secured to the interior of each ear-covering member, said rim being large enough to encircle the user's ear and deep enough to form a seal between the ear-covering member and the user's head.

2. The ear protector of claim 1 wherein the resilient rim is provided by a molded cup of a resilient material projecting inwardly from the ear-covering member.

3. The ear protector of claim 2 further including a layer of absorbent material disposed within the area encircled by the resilient rim, to trap water which may leak passed the resilient rim.

* * * * *